United States Patent
Minami

(10) Patent No.: US 9,022,589 B2
(45) Date of Patent: May 5, 2015

(54) SIMULATED SUNLIGHT IRRADIATION APPARATUS

(75) Inventor: Kohji Minami, Osaka (JP)

(73) Assignee: Sharp Kabushiki Kaisha, Osaka (JP)

(*) Notice: Subject to any disclaimer, the term of this patent is extended or adjusted under 35 U.S.C. 154(b) by 113 days.

(21) Appl. No.: 13/985,439

(22) PCT Filed: Feb. 10, 2012

(86) PCT No.: PCT/JP2012/053184
§ 371 (c)(1),
(2), (4) Date: Aug. 14, 2013

(87) PCT Pub. No.: WO2012/132583
PCT Pub. Date: Oct. 4, 2012

(65) Prior Publication Data
US 2014/0009901 A1    Jan. 9, 2014

(30) Foreign Application Priority Data
Mar. 28, 2011 (JP) ................... 2011-071135

(51) Int. Cl.
F21V 9/02 (2006.01)
F21S 8/00 (2006.01)
F21V 8/00 (2006.01)
G01N 17/00 (2006.01)

(52) U.S. Cl.
CPC ............... *F21S 8/006* (2013.01); *G01N 17/002* (2013.01); *G02B 6/0026* (2013.01); *G02B 6/005* (2013.01)

(58) Field of Classification Search
CPC ..... F21S 8/006; G02B 6/0026; G02B 6/0028; G02B 6/0068; G02B 6/007
USPC .......................................... 362/1–2, 608, 610
See application file for complete search history.

(56) References Cited

U.S. PATENT DOCUMENTS

| | | |
|---|---|---|
| 2006/0152777 A1 | 7/2006 | Iwasaki |
| 2006/0238750 A1 | 10/2006 | Shimotomai |
| 2009/0190072 A1 | 7/2009 | Nagata et al. |
| 2010/0302477 A1 | 12/2010 | Ohmi et al. |
| 2012/0014085 A1 | 1/2012 | Minami |
| 2012/0134131 A1 | 5/2012 | Nakamura et al. |
| 2012/0275132 A1 | 11/2012 | Minami et al. |

FOREIGN PATENT DOCUMENTS

| | | |
|---|---|---|
| JP | 08-235903 | 9/1996 |
| JP | 2002-048704 | 2/2002 |
| JP | 2004-191702 | 7/2004 |
| JP | 2006-216619 | 8/2006 |
| JP | 2007-158379 | 6/2007 |
| JP | 2007-334325 | 12/2007 |
| JP | 2010-287510 | 12/2010 |
| JP | 4723038 | 7/2011 |
| WO | 2010/143329 | 12/2010 |

*Primary Examiner* — Jason Moon Han
(74) *Attorney, Agent, or Firm* — Keating & Bennett, LLP

(57) ABSTRACT

A simulated sunlight irradiation apparatus (100) has transmittance adjustment members (13a and 13b) provided above an irradiation surface of a light guide plate (10) and in the vicinity of either incident face of the light guide plate (10) on which simulated sunlight is incident. The transmittance adjustment members (13a and 13b) adjust the transmittance of light in a portion of a wavelength band of simulated sunlight that is emitted from the irradiation surface of the light guide plate (10), thus bringing about improvement in spectral coincidence of the simulated sunlight. This provides a simulated sunlight irradiation apparatus that can radiate simulated sunlight with high spectral coincidence.

11 Claims, 6 Drawing Sheets

SIMULATED SUNLIGHT IRRADIATION APPARATUS

CROSS-REFERENCE TO RELATED APPLICATIONS

This application is a National Phase application filed under 35 USC 371 of PCT International Application No. PCT/JP2012/053184 with an International Filing Date of Feb. 10, 2012, which claims under 35 U.S.C. §119(a) the benefit of Japanese Application No. 2011-071135, filed Mar. 28, 2011, the entire contents of which are incorporated herein by reference.

TECHNICAL FIELD

The present invention relates to a simulated sunlight irradiation apparatus that radiates simulated sunlight.

BACKGROUND ART

Solar batteries have been recognized as important as clean energy sources, and as such, have been in increasing demand. Solar batteries are used in a wide range of fields from power energy sources for large machinery to small-sized power sources for precision electronics. In order for solar batteries to be widely used in a variety of fields, it is necessary that the characteristics, in particular output characteristics, of the solar batteries be accurately measured. Unless the output characteristics are not accurately measured, there will be various inconveniences on the side of solar-battery users. Under such circumstances, there is a particular demand for a technology which can be used for inspections of, measurements of, and experiments on solar batteries and which can irradiate a large area with high-precision simulated sunlight.

Accordingly, a simulated sunlight irradiation apparatus has recently been under development as an apparatus that can radiate simulated sunlight. In general, the simulated sunlight irradiation apparatus is used for measuring the output characteristics of a panel-shaped solar battery by irradiating a receiving surface of the solar battery with artificial light (simulated sunlight) of uniform illuminance.

A major requirement for simulated sunlight is getting closer in emission spectrum to reference sunlight (as defined by the Japanese Industrial Standards: JIS C8941). In other words, the simulated sunlight irradiation apparatus is required, in particular, to be high in spectral coincidence. The term "spectral coincidence" here means the proximity of simulated sunlight in spectrum to the reference sunlight. However, the simulated sunlight irradiation apparatus is only provided with light source lamps in the form of dots or lines (dot-like light sources or linear light sources). This problematically makes it extremely difficult to irradiate the whole (or entire) receiving surface, which is in the form of a plane, of a solar battery with simulated sunlight of uniform illuminance.

In order to solve this problem, Patent Literatures 1 and 2 each disclose a technology for correcting nonuniformity in illuminance of a simulated sunlight irradiation apparatus.

Patent Literature 1 discloses a simulated sunlight irradiation apparatus (solar simulator) having a halogen lamp and a xenon lamp provided in separate chambers adjacent to each other. Specifically, the simulated sunlight irradiation apparatus has a dedicated optical filter provided in an open section above each of the lamps. This causes the receiving surface of a solar battery to be irradiated with simulated sunlight due to lighting of the lamps below. Furthermore, the simulated sunlight irradiation apparatus has a reflective plate in each of the chambers in which the respective lamps are provided. This makes it possible to correct nonuniformity in illuminance among the lamps.

Meanwhile, Patent Literature 2 discloses a simulated sunlight irradiation apparatus (solar simulator) that has a light intensity adjustment member provided for each of those zones into which the receiving surface of a solar battery is imaginarily divided. Specifically, the simulated sunlight irradiation apparatus has three types of light intensity adjustment member having different light-blocking rates. The light intensity adjustment members have their light-blocking rates set so that with reference to the illuminance of the darkest zone of the receiving surface of a solar battery, the illuminances of the other zones are made the same as the illuminance of the darkest zone. This makes it possible to make the illuminance of the light sources in one zone of the receiving surface substantially the same as that in another zone of the receiving surface.

CITATION LIST

Patent Literature 1

Japanese Patent Application Publication, Tokukai, No. 2002-048704 (Publication Date: Feb. 15, 2002)

Patent Literature 2

Japanese Patent Application Publication, Tokukai, No. 2006-216619 (Publication Date: Aug. 17, 2006)

SUMMARY OF INVENTION

Technical Problem

However, these conventional simulated sunlight irradiation apparatuses are problematically low in spectral coincidence.

Specifically, the simulated sunlight irradiation apparatus of Patent Literature 1 is configured such that a lamp that emits xenon light and a lamp that emits halogen light are located in different places. This undesirably causes a degree of mixture of the xenon light and the halogen light to slightly vary, for example, due to a direction in which light from each of the lamps travels. This results in a phenomenon in which simulated sunlight varies in irradiation spectrum from irradiated site to irradiated site. This makes it difficult to make spectral coincidence uniform over the entire irradiated surface, thus making it impossible to configure the simulated sunlight irradiation apparatus to be high in spectral coincidence.

Further, Patent Literature 2 merely discloses simply providing a light intensity adjustment member in each of those zones into which the receiving surface is imaginarily divided. However, Patent Literature 2 is completely silent about an influence that is exerted on the spectral distribution by providing light intensity adjustment members having different transmittances. That is, in actuality, the simulated sunlight irradiation apparatus of Patent Literature undesirably varies in transmittance among various wavelength bands in each zone. This makes it impossible to radiate simulated sunlight with high spectral coincidence. As such, the simulated sunlight irradiation apparatus of Patent Literature 2 cannot be adapted to raise spectral coincidence, which requires adjustment of transmittance through control of transmittance for each wavelength band.

The present invention has been made in view of the conventional problems, and it is an object of the present invention to provide a simulated sunlight irradiation apparatus that can radiate simulated sunlight with high spectral coincidence.

Solution to Problem

In order to solve the foregoing problems, a simulated sunlight irradiation apparatus according to the present invention includes: a first light source which radiates a first ray of light; a second light source which radiates a second ray of light having a spectral distribution that is different from a spectral distribution of the first ray of light; a first optical filter which controls a transmittance of the first ray of light; a second optical filter which controls a transmittance of the second ray of light; a photoselection section which receives the first ray of light whose transmittance has been controlled by the first optical filter and the second ray of light whose transmittance has been controlled by the second optical filter, and which emits simulated sunlight by mixing together a ray of light selected from the first ray of light thus received and a ray of light selected from the second ray of light thus received; a light guide plate which receives the simulated sunlight emitted from the photoselection section; a light extraction section which takes out, to an irradiation surface of the light guide plate, the simulated sunlight received by the light guide plate; and a transmittance adjustment member which is located closer to the irradiation surface of the light guide plate than the light extraction section is, and which adjusts a transmittance of light in a portion of a wavelength band of simulated sunlight that is emitted from the irradiation surface of the light guide plate.

According to the foregoing invention, when the first ray of light emitted from the first light source enters the first optical filter, the transmittance of the first ray of light is controlled by the first optical filter. Similarly, when the second ray of light emitted from the second light source enters the second optical filter, the transmittance of the first ray of light is controlled by the first optical filter. Then, the rays of light, whose transmittances have been controlled by the first and second optical filters, respectively, enter the photoselection section. In this way, emission spectra of the first and second rays of light are adjusted by the first and second optical filters and the photoselection section. As a result, simulated sunlight that is proximate in emission spectrum to reference sunlight is emitted from the photoselection section. Therefore, simulated sunlight that is high in spectral coincidence enters the light guide plate.

Furthermore, according to the foregoing invention, the transmittance adjustment member, located at the side of the irradiation surface of the light guide plate, adjusts a transmittance of light in a portion of a wavelength band of simulated sunlight that is emitted from the irradiation surface of the light guide plate. In this way, the transmittance adjustment member brings about improvement in spectral coincidence of simulated sunlight. This makes it possible to provide a simulated sunlight irradiation apparatus that can radiate simulated sunlight with high spectral coincidence.

Additional objects, features, and strengths of the present invention will be made clear by the description below. Further, the advantages of the present invention will be evident from the following explanation in reference to the drawings.

Advantageous Effects of Invention

As described above, a simulated sunlight irradiation apparatus according to the present invention is configured to include a transmittance adjustment member which is located closer to the irradiation surface of the light guide plate than the light extraction section is, and which adjusts a transmittance of light in a portion of a wavelength band of simulated sunlight that is emitted from the irradiation surface of the light guide plate. This brings about an effect of making it possible to provide a simulated sunlight irradiation apparatus that can radiate simulated sunlight with high spectral coincidence.

DESCRIPTION OF EMBODIMENTS (Configuration of a Simulated Sunlight Irradiation Apparatus 100)

Figure 1:
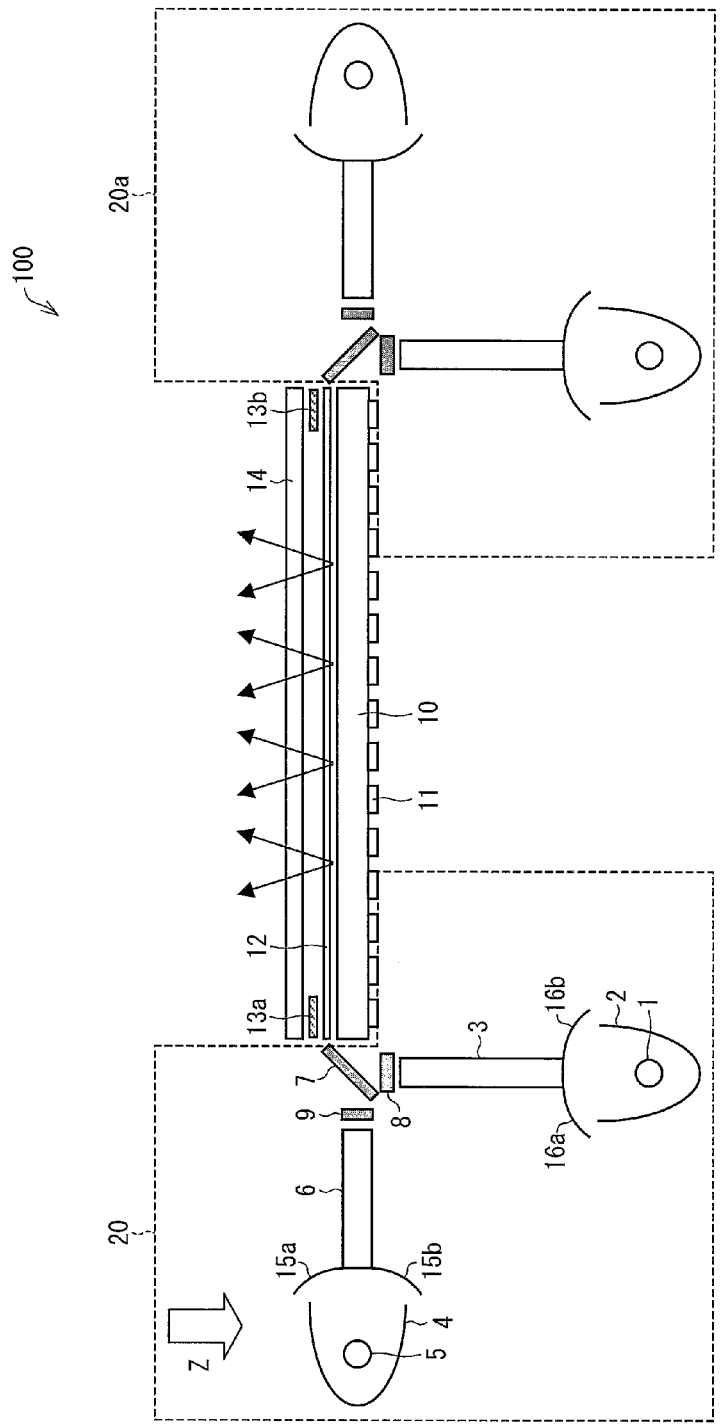
FIG. 1 is a side view showing a configuration of a main part of a simulated sunlight irradiation apparatus according to an embodiment of the present invention.

An embodiment of the present invention is described below with reference to the drawings. FIG. 1 is a diagram showing a configuration of a main part of a simulated sunlight irradiation apparatus 100 according to an embodiment of the present invention.

The simulated sunlight irradiation apparatus 100 includes a light guide plate 10, light introduction sections 20 and 20a, a light extraction section 11, a prism sheet 12, transmittance adjustment members 13a and 13b, and a protective plate 14. The simulated sunlight irradiation apparatus 100 emits simulated sunlight (indicated by arrows in the drawing) through an irradiation surface (upper surface) of the light guide plate 10 onto an object to be irradiated, such as a solar battery. The simulated sunlight irradiation apparatus 100 is described in detail below. Let it be assumed throughout the following description that the irradiation surface of the light guide plate 10 is an upper side and a (back) surface of the light guide plate 10 opposite the irradiation surface is a lower side.

The light guide plate 10 is provided between the light introduction sections 20 and 20a placed opposite each other. The light guide plate 10 radiates, through an irradiation surface (upper surface) of the light guide plate 10, simulated sunlight with which the light introduction sections 20 and 20a irradiate both side surfaces of the light guide plate 10.

The light extraction section 11 is provided on a lower surface (back surface) of the light guide plate 10. The light extraction section 11 takes out, to the irradiation surface of the light guide plate 10, the simulated sunlight emitted from the light introduction sections 20 and 20a. Specifically, light (simulated sunlight) emitted from the light introduction sections 20 and 20a and having entered the light guide plate 10 propagates through the light guide plate 10. In so doing, light having struck the light extraction section 11 is directed toward the irradiation surface of the light guide plate 10. This makes it possible to uniformly radiate simulated sunlight through a wider irradiation surface. It should be noted that the light extraction section 11 can be constituted, for example, by scatterers, which scatter simulated sunlight inside of the light guide plate 10 so that the simulated sunlight can be guided toward the irradiation surface. Further, by changing the pattern of scatterers, nonuniformity in illuminance of the simulated sunlight can be corrected. This makes it possible to radiate uniform simulated sunlight with less nonuniformity in illuminance.

The prism sheet 12, the transmittance adjustment members 13a and 13b, and the protective plate 14 are placed in this order above the irradiation surface of the light guide plate. The prism sheet 12 applies the effect of refraction of light to create a large number of components of irradiation light that is radiated in a direction perpendicular to the irradiation surface of the light guide plate 10. That is, the prism sheet 12 is a member that causes the light extracted by the light extraction section 11 from the light guide plate 10 to be refracted in a direction perpendicular to the irradiation surface of the light guide plate 10. The transmittance adjustment members 13a and 13b cause a change in transmittance of light in a portion of a wavelength band of the simulated sunlight that is radiated from the irradiation surface of the light guide plate 10. The transmittance adjustment members 13a and 13b will be described in detail later. The protective plate 14 covers the irradiation surface of the light guide plate 10 so as to protect the light guide plate 10.

The light introduction sections 20 and 20a are provided at both side surfaces of the light guide plate 10. In the simulated sunlight irradiation apparatus 100, the light introduction sections 20 and 20a emit the simulated sunlight to to both edges of the light guide plate 10. This makes it possible to emit simulated sunlight of a higher light intensity (illuminance) from the irradiation surface. However, it is possible to provide only the light guide section 20 at one edge of the light guide plate 10 instead of providing the light introduction sections 20 and 20a at both edges of the light guide plate 10. That is, the simulated sunlight irradiation apparatus 100 does not need to include the light introduction section 20a. It should be noted that the light introduction section 20a includes optical components identical to those which the light introduction section 20 includes.

Specifically, the light introduction section 20 includes: a xenon light source (xenon lamp) 1 (first light source); an elliptic mirror 2 (first light-collecting element; directivity control section); a tapered coupler 3 (tapered light guide member; directivity control section); a halogen light source (halogen lamp) 4 (second light source); an elliptic mirror 5 (second light-collecting element); a tapered coupler 6 (tapered light guide member; directivity control section); a wavelength-mixing filter 7 (photoselection section); optical filters 8 and 9; and reflective plates 15a, 15b, 16a, and 16b (directivity control section).

The light introduction section 20 generates simulated sunlight by using the wavelength-mixing filter 7 to mix rays of light emitted from the xenon light source 1 and the halogen light source 4, respectively, and irradiates an end face (incident face) of the light guide plate 10 with the simulated sunlight.

Specifically, the xenon light source 1 and the halogen light source 4 are light sources provided in the simulated sunlight irradiation apparatus 100. The xenon light source 1 and the halogen light source 4 radiate rays of light having spectral distributions that are necessary for generating simulated sunlight. The rays of light radiated from the xenon light source 1 and the halogen light source 4 have different spectral distributions from each other. The xenon light source 1 mostly radiates a short-wavelength component of light that is necessary for simulated sunlight. Meanwhile, the halogen light source 4 mostly radiates a long-wavelength component of light that is necessary for simulated sunlight.

The xenon light source 1 is surrounded by the elliptic mirror 2 (reflecting member) except on a side facing in a direction of emission toward the tapered coupler 3, and the halogen light source 4 is surrounded by the elliptic mirror 5 (reflecting member) except on a side facing in a direction of emission toward the tapered coupler 6. This causes rays of light emitted from the xenon light source 1 and the halogen light source 4 but not directed toward the tapered couplers 3 and 6 to be reflected by the elliptic mirrors 2 and 5 and emitted toward the tapered couplers 3 and 6, respectively. That is, the elliptic mirrors 2 and 5 collect the rays of light outputted from the respective light sources and cause the rays of light to be emitted. As a result, the rays of light emitted directly from the xenon light source 1 and the halogen light source 4 and the rays of light reflected by the elliptic mirrors 2 and 5 are emitted toward the tapered couplers 3 and 6, respectively. Therefore, the rays of output light from the xenon light source 1 and the halogen light source 4 are effectively utilized.

The tapered couplers 3 and 6 are optical elements provided in the light introduction section 20. The tapered coupler 3 is provided between the xenon light source 1 and the wavelength-mixing filter 7, and the tapered coupler 6 is provided between the halogen light source 4 and the wavelength-mixing filter 7. One end of the tapered coupler 3 is located in proximity to the xenon light source 1, and the other end of the tapered coupler 3 is located in proximity to the wavelength-mixing filter 7. One end of the tapered coupler 6 is located in proximity to the halogen light source 4, and the other end of the tapered coupler 6 is located in proximity to the wavelength-mixing filter 7. The tapered couplers 3 and 6 are arranged so that a direction of emission of light from the tapered coupler 3 (light from the xenon light source 1) and a direction of emission of light from the tapered coupler 6 (light from the halogen light source 4) form an angle of 90 degrees.

The light introduction section 20 includes the optical filters 8 and 9 in order to cause simulated sunlight to approximate in emission spectrum to reference sunlight. The optical filters 8 and 9 are optical elements that adjust the spectra (control the transmittances) of the rays of light emitted from the xenon light source 1 and the halogen light source 4 (tapered couplers 3 and 6), respectively. The optical filters 8 and 9 are generally referred to as "air-mass filters (spectrum adjustment filters)".

Specifically, the optical filter 8 is provided in proximity to an emitting face of the tapered coupler 3, which corresponds to the xenon light source 1. The optical filter 8 adjusts the spectral distribution of xenon light emitted from the tapered coupler 3. Similarly, the optical filter 9 is provided in proximity to an emitting face of the tapered coupler 6, which corresponds to the halogen light source 4. The optical filter 9 adjusts the spectral distribution of halogen light emitted from the tapered coupler 6. This causes the rays of light whose spectra have been adjusted by the optical filters 8 and 9, respectively, to enter the wavelength-mixing filter 7.

The wavelength-mixing filter 7 has a function of wavelength selection. That is, the wavelength-mixing filter 7 selects (extracts) rays of light that are necessary for simulated sunlight from the rays of light radiated from the xenon light source 1 and the halogen light source 4, and synthesizes simulated sunlight by mixing the rays of light thus selected. Specifically, the wavelength-mixing filter 7 reflects light of a wavelength less than a predetermined wavelength (closer to the short-wavelength side than the predetermined wavelength) and transmits light of a wavelength equal to or greater than the predetermined wavelength (closer to the long-wavelength side than the predetermined wavelength). In other words, the wavelength-mixing filter 7 has a function of transmitting light on the long-wavelength side that is necessary for simulated sunlight and reflecting light on the short-wavelength side, and synthesizes simulated sunlight by mixing the light on the long-wavelength side and the light on the short-wavelength side.

Specifically, the wavelength-mixing filter 7 receives a ray of output light (first rays of light) from the xenon light source 1 and a ray of output light (second ray of light) from the halogen light source 4. Then, the wavelength-mixing filter 7 selects necessary components (spectra) of light from the rays of output light thus received, and synthesizes simulated sunlight by mixing the components of light thus selected.

More specifically, the ray of output light from the xenon light source 1 mostly contains a component on the short-wavelength side that is necessary for simulated sunlight; meanwhile, the ray of output light from the halogen light source 4 mostly contains a component on the long-wavelength side that is necessary for simulated sunlight. Since the wavelength-mixing filter 7 has its boundary wavelength set within a range of 600 to 800 nm, the wavelength-mixing filter 7 reflects light of a wavelength less than the boundary wavelength and transmits light of a wavelength equal to or greater than the boundary wavelength. That is, out of the ray of output light from the xenon light source 1, only light of a wavelength less than the boundary wavelength (component of light on the short-wavelength side) is reflected by the wavelength-mixing filter 7. Meanwhile, out of the ray of output light from the halogen light source 4, only light of a wavelength equal to or greater than the boundary wavelength (component of light on the long-wavelength side) is transmitted by the wavelength-mixing filter 7.

For example, let it be assumed that a component of light from the xenon light source 1 whose wavelength is less than 700 nm is used and a component of light from the halogen light source 4 whose wavelength is 700 nm or greater is used. In this case, the wavelength-mixing filter 7 has a boundary wavelength of 700 nm between reflection and transmission. That is, the wavelength-mixing filter 7 has ability to reflect short-wavelength light having a wavelength of less than 700 nm and transmit long-wavelength light having a wavelength of 700 nm or greater. This allows only those components of light of wavelengths which are necessary for simulated sunlight to be selected by the wavelength-mixing filter 7. Then, the components of light are combined into simulated sunlight to be emitted. It should be noted that it is possible to set any boundary wavelength between light that the wavelength-mixing filter 7 reflects and light that the wavelength-mixing filter 7 transmits. Furthermore, the wavelength-mixing filter 7 may be a wavelength-dependent mirror or filter, usable examples of which include a cold mirror, a hot mirror, etc.

In this way, the wavelength-mixing filter 7 generates simulated sunlight by extracting a short-wavelength component of light which is contained in the ray of output light from the xenon light source 1 and which is necessary for the synthesis of simulated sunlight and a long-wavelength component of light which is contained in the ray of output light from the halogen light source 4 and which is necessary for the synthesis of simulated sunlight. In so doing, the wavelength-mixing filter 7 eliminates a long-wavelength component of light from the xenon light source 1 whose spectrum has not been controlled and, similarly, eliminates a short-wavelength component of light from the halogen light source 2 whose spectrum has not been controlled.

This makes it possible to cause the simulated sunlight to approximate in emission spectrum to the reference sunlight.

The elliptic mirror 2 is outfitted with the reflecting plates 16a and 16b, and the elliptic mirror 4 is outfitted with the reflecting plates 15a and 15b. The reflecting plates 16a and 16b surround an incident face of the tapered coupler 3. Similarly, the reflecting plates 15a and 15b surround an incident face of the tapered coupler 6. This causes rays of light emitted from the xenon light source 1 and the halogen light source 4 toward the tapered couplers 3 and 6 but having not entered the incident faces to be reflected by the reflecting plates 16a and 16b and the reflecting plates 15a and 15b and emitted again toward the tapered couplers 3 and 6, respectively. That is, the reflecting plates 16a and 16b and the reflecting plates 15a and 15b collect the rays of light outputted from the respective light sources and cause the rays of light to be emitted. As a result, the rays of light emitted directly from the xenon light source 1 and the rays of light reflected by the reflecting plates 16a and 16b and the elliptic mirror 2 are emitted toward the tapered coupler 3, and the rays of light emitted directly from the halogen light source 4 and the rays of light reflected by the reflecting plates 15a and 15b and the elliptic mirror 5 are emitted toward the tapered coupler 6. Therefore, the rays of output light from the xenon light source 1 and the halogen light source 4 are effectively utilized.

(Directivity of the Simulated Sunlight Irradiation Apparatus 100)

Since the xenon light source 1 and the halogen light source 4 are nondirectional light sources, the rays of output light from the respective light sources are rays of diffusion light that spread. For this reason, it is preferable that the directivity of the rays of output light from the respective light sources be controlled so that each of the rays of light enters the wavelength-mixing filter 7 at a predetermined angle of incidence.

In the simulated sunlight irradiation apparatus 100, the ray of light emitted from the xenon light source 1 has its radiation directivity controlled by the elliptic mirror 2. Furthermore, the ray of light emitted from the xenon light source 1 also has its radiation directivity controlled by the tapered coupler 3. The ray light whose directivity has been controlled passes through the optical filter 8, which adjusts the emission spectrum, and then enters the wavelength-mixing filter 7. Out of the ray of light having entered the wavelength-mixing filter 7, light of a wavelength less than the boundary wavelength (closer to the short-wavelength side than the predetermined wavelength) is reflected by the wavelength-mixing filter 7.

Meanwhile, the ray of light emitted from the halogen light source 4 has its radiation directivity controlled by the elliptic mirror 5. Furthermore, the ray of light emitted from the halogen light source 4 also has its radiation directivity controlled by the tapered coupler 6. The ray light whose directivity has been controlled passes through the optical filter 8, which adjusts the emission spectrum, and then enters the wavelength-mixing filter 7. Out of the ray of light having entered the wavelength-mixing filter 7, light of a wavelength equal to or greater than the boundary wavelength (closer to the long-wavelength side than the predetermined wavelength) is transmitted by the wavelength-mixing filter 7.

The wavelength-mixing filter 7 mixes together the ray of light emitted from the xenon light source 1 and having its directivity controlled and the ray of light emitted from the halogen light source 4 and having its directivity controlled. In the simulated sunlight irradiation apparatus 100, the xenon light source 1 and the halogen light source 4 are used. The irradianace of the xenon light source 1 on the short-wavelength side is comparatively close to the irradiance characteristics of the reference sunlight (as defined by the JIS), and the irradiance of the halogen light source 4 in an infrared region (which ranges mainly from 700 nm to 1100 nm) is close to being substantially constant. This makes it possible to raise spectral coincidence (to Class MS as defined by the JIS) by using the xenon light source 1 and the halogen light source 4. Moreover, the rays of light transmitted or reflected by the wavelength-mixing filter 7 and directed toward the light guide plate 10 have their spectral coincidence raised by the optical filters 8 and 9. That is, their spectral distributions are close to that of the reference sunlight, so that their spectral coincidence, which indicates their deviations from the reference sunlight, is almost as high as ±5%. Therefore, the light guide plate 10 receives simulated sunlight with high spectral coincidence. This allows the light guide plate 10 to radiate light with good spectral coincidence.

It should be noted that in the simulated sunlight irradiation apparatus 100, the xenon light source 1 and the halogen light source 4 are used as light sources from which simulated sunlight is obtained. However, the types of light sources and the combination of the light sources are not to be so limited, but can be optionally selected so that the resulting simulated sunlight is proximate or identical to the reference sunlight. For example, it is possible to use rod-shaped light sources and the like instead of using the xenon light source 1 and the halogen light source 4.

Further, in the simulated sunlight irradiation apparatus 100, the elliptic mirror 2 is outfitted with the reflecting plates 16a and 16b, and the elliptic mirror 5 is outfitted with the reflecting plates 15a and 15b. This causes rays of light having not entered the tapered couplers 3 and 6 to be reflected by the reflecting plates 16a and 16b and the reflecting plates 15a and 15b and then reflected again by the elliptic mirrors 2 and 5 to enter the tapered couplers 3 and 6, respectively. This makes it possible to effectively utilize the rays of output light from the xenon light source 1 and the halogen light source 4, thus making it possible to selectively take out highly directional light.

Figure 2:
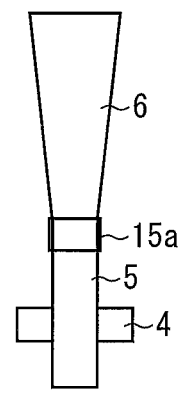
FIG. 2 is a diagram showing part of a light introduction section of the simulated sunlight irradiation apparatus of FIG. 1.

FIG. 2 is a diagram showing part of the light introduction section 20 of the simulated sunlight irradiation apparatus 100. That is, FIG. 2 is a top view of the light introduction section 20 as seen from the direction of the arrow Z in FIG. 1.

As shown in FIG. 2, the tapered coupler 6 of the simulated sunlight irradiation apparatus 100 is in a tapered shape (trapezoidal shape) having a pair of opposing faces that become closer to each other toward one end. The tapered coupler 3 is also in the same shape. That is, each of the tapered couplers 3 and 6 gradually becomes larger in width (cross-sectional area) from the incident face toward the emitting face of that tapered coupler. Such a structure brings about improvement in directivity (angle of radiation) of the rays of light emitted from the xenon light source 1 and the halogen light source 4, as they are repeatedly reflected by the side surfaces of the tapered couplers 3 and 6, respectively. This causes rays of light of uniform directivity (having their angles of radiation controlled) to be emitted from the emitting faces of the tapered couplers 3 and 6. It should be noted that the angles of radiation of the rays of light that are emitted from the tapered couplers 3 and 6 are controlled in accordance with the angles of inclination of the side surfaces of the tapered couplers 3 and 6 and the lengths along which the rays of light travels through the tapered couplers 3 and 6, respectively.

Further, use of the tapered couplers 3 and 6 causes all of the rays of light emitted from the xenon light source 1 and the halogen light source 4 to propagate through the tapered couplers 3 and 6, respectively. Further, use of the tapered couplers 3 and 6 causes the rays of light emitted from the xenon light source 1 and the halogen light source 4 to be uniform in traveling direction (directivity), and causes the uniform rays of light to enter the wavelength-mixing filter 7 with low loss. The tapered couplers 3 and 6 can be made, for example, of quartz etc.

The advantage of making the rays of light uniform in directivity by using the tapered couplers 3 and 6 is associated with the structures of the optical filters 8 and 9. Specifically, each of the optical filters 8 and 9 has a structure in which a plurality of thin films are joined on top of each other. For this reason, a greater shift in the angle of incidence on each of the optical filters 8 and 9 from normal incidence on that optical filter leads to a change in transmittance characteristic. That is, incident of a ray of light to each of the optical filters 8 and 9 with poor directivity leads to generation of simulated sunlight having a spectral distribution that is different from that of the reference sunlight. However, making the rays of light uniform in directivity by using the tapered couplers 3 and 6 makes it possible to generate simulated sunlight that is close in spectral distribution to the reference sunlight.

Similarly, the wavelength-mixing filter 7 also has a structure in which a plurality of thin films are joined on top of each other. For this reason, a difference between angles of incidence on the wavelength-mixing filter 7 leads to a change in transmittance characteristic or reflectance characteristic. That is, incident of rays of light to the wavelength-mixing filter 7 with poor directivity leads to generation of simulated sunlight having a spectral distribution that is different from that of the reference sunlight. However, by making the rays of light uniform in directivity by using the tapered couplers 3 and 6, a change in transmission characteristic or reflection characteristic at the wavelength-mixing filter 7 is suppressed. This makes it possible to generate simulated sunlight that is close in spectral distribution to the reference sunlight.

Since the simulated sunlight irradiation apparatus 100 includes the tapered couplers 3 and 6, the directivities of xenon light and halogen light are controlled so that the xenon light enters the optical filter 8 at a predetermined angle of incidence and enters the wavelength-mixing filter 7 at a predetermined angle of incidence and the halogen light enters the optical filter 9 at a predetermined angle of incidence and enters the wavelength-mixing filter 7 at a predetermined angle of incidence. This prevents the xenon light and the halogen light from losing their light intensity by the time they arrive at the wavelength-mixing filter 7. Furthermore, since the tapered couplers 3 and 6 make the rays of light uniform in directivity, it is possible to generate simulated sunlight that is close in spectral distribution to the reference sunlight. This makes it possible to irradiate an irradiated object with simulated sunlight that is closer in illuminance (light intensity) and emission spectrum to the reference sunlight. It should be noted that with just one of the couplers 3 and 6, it is possible to control the directivity of xenon light or halogen light so that the light can enter the wavelength-mixing filter 7 at a predetermined angle of incidence.

It is preferable that the control of the directivities of rays of light by the tapered couplers 3 and 6 be carried out by causing the rays of light to propagate through the tapered couplers 3 and 6, respectively, in such a manner that the maximum angle of radiation is 30 degrees or smaller. This causes each of the rays of light propagating through the tapered couplers 3 and 6 from the incident face to the emitting face to increase in proportion of a component that is emitted with a directivity of 0 degree (i.e., in a direction perpendicular to the emitting face of the tapered coupler 3 or 6). Similarly, it is also preferable that the directions of propagation of the rays of light be set so that the elliptic mirrors 2 and 5 collect the rays of light from the xenon light source 1 and the halogen light source 4, respectively, in such a manner that the angle of radiation is 30 degrees or smaller with respect to the normal incidence (0-degree incidence) on the incident end of the tapered coupler 3 or 6.

(Features of the Simulated Sunlight Irradiation Apparatus 100)

The simulated sunlight irradiation apparatus 100 faces a problem in introducing simulated sunlight emitted from the wavelength-mixing filter 7 into the light guide plate 10. Specifically, of the simulated sunlight that enters the light guide plate 10, light whose directivity is poor (whose angle of radiation is close to 30 degrees) increases in component that does not satisfy the total reflection condition for the light to propagate through the light guide plate 10, when after the light has entered the light guide plate 10 there is a shift in propagation angle inside of the light guide plate 10 at which the light propagates through the light guide plate 10. This makes it easy for the light to go out of the light guide plate 10. Further, the closer the angle of radiation is to 30 degrees, the more likely the wavelength-mixing filter 7 is to reflect or transmit the light at a wavelength of 700 nm at a different transmittance than a design value. This causes the actual transmittance of light of 650 nm to 750 nm at the wavelength-mixing filter 7 to be higher or lower than the design transmittance. Such a shift in transmittance is a result of an error in manufacture of the film structure of the wavelength-mixing filter 7.

As a result, simulated sunlight that is radiated from the irradiation surface of the light guide plate 10 in the vicinity of the incident face of the light guide plate 10 (light that goes out of the light guide plate 10) increases in proportion of light whose transmittance control has deviated from the design. In the simulated sunlight irradiation apparatus 100, the transmittance of light of a wavelength of 650 nm to 750 nm in particular tends to deviate from the design value. For this reason, even when the spectral coincidence, which indicates proximity in spectrum to the reference sunlight, takes on a satisfactory value in the center of the light guide plate 10, it is not as good in the vicinity of the incident face (incident end) of the light guide plate 10.

In order to overcome this problem, the simulated sunlight irradiation apparatus 100 includes the transmittance adjustment members 13a and 13b. The transmittance adjustment members 13a and 13b are located closer to the irradiation surface of the light guide plate 10 than the light extraction section 11 is. Furthermore, the transmittance adjustment members 13a and 13b adjust the transmittance of light in a portion of a wavelength band of the simulated sunlight that is radiated from the irradiation surface, thereby bringing about improvement in spectral coincidence of the simulated sunlight. This makes it possible to radiate simulated sunlight that is high in spectral coincidence.

The transmittance adjustment members 13a and 13b need only be located closer to the irradiation surface of the light guide plate 10 than the light extraction section 11 is. However, it is preferable that the transmittance adjustment members 13a and 13b be located in the vicinity of either incident face of the light guide plate 10 where there are likely to be a change in transmittance (transmittance characteristic) and therefore a decrease in spectral coincidence. For example, it is preferable that the transmittance adjustment members 13a and 13b be provided above the irradiation surface (emitting face) of the light guide plate 10. Furthermore, it is preferable that the transmittance adjustment members 13a and 13b be set to adjust the transmittance of light in a wavelength band of 650 nm to 750 nm where there is likely to be a deviation from the design value. For example, the transmittance adjustment members 13a and 13b can each be formed from an optical multi-layer film having ability to reduce the light intensity of light in the wavelength band by 3 to 5% (3% or more and 5% or less). This allows the transmittance adjustment members 13a and 13b to adjust the transmittance to bring about improvement in spectral coincidence.

Figure 3:
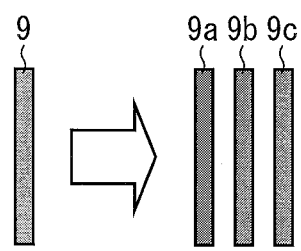
FIG. 3 is a diagram showing an example configuration of an optical filter of the simulated sunlight irradiation apparatus of FIG. 1.

Incidentally, the simulated sunlight irradiation apparatus 100 of FIG. 1 includes, for each separate light source, the optical filters 8 and 9 each constituted by a single filter. However, the optical filters 8 and 9 may each be constituted by a plurality of filters. For example, FIG. 3 is a diagram showing an example configuration of the optical filter 9 of the simulated sunlight irradiation apparatus 100. Such an optical filter 9 as that shown in FIG. 3 which is constituted by a plurality of optical filters (namely three optical filters 9a, 9b, and 9c in FIG. 3) makes it possible to adjust spectra in finer wavelength bands. This makes it possible to generate simulated sunlight that is more similar in spectral distribution to the reference sunlight.

TABLE 1

|  | Optical filter 9a | Optical filter 9b | Optical filter 9c |
| --- | --- | --- | --- |
| Transmittance adjustment wavelength bands | 750 nm to 850 nm | 900 nm to 1000 nm | 700 nm to 1100 nm |

Further, Table 1 shows the transmission characteristics (transmittance adjustment wavelength bands) of the optical filters 9a, 9b, and 9c. Here, the transmittance adjustment wavelength band of the optical filter 9a ranges from 750 nm to 850 nm, which is close to the boundary wavelength of 700 nm of the wavelength-mixing filter 7. For this reason, due to the influence of a shift in optical characteristic of the optical filter 9a, a spectral shift may occur in a wider portion of the wavelength band in which the halogen light source 4 is used. In this case, there may be a change in transmittance in the wavelength range of 650 nm to 850 nm and therefore a decrease in spectral coincidence. As a result, the transmittance adjustment wavelength bands of the transmittance adjustment members 13a and 13b become wider than 650 nm to 750 nm, which makes it necessary to improve the spectral coincidence by adjusting the transmittance in the range of 650 nm to 750 nm.

Figure 4:
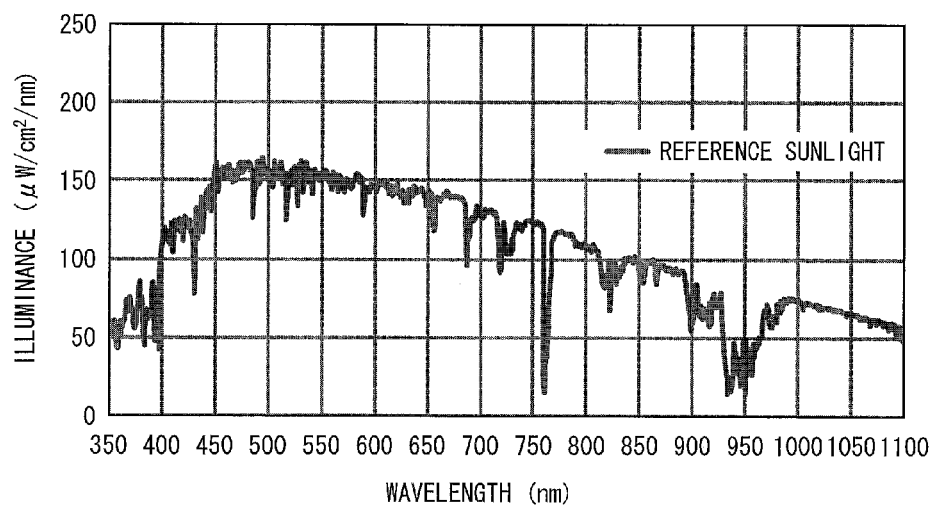
FIG. 4 is a graph showing a spectrum of reference sunlight.

Meanwhile, FIG. 4 is a graph showing a spectrum of the reference sunlight. The reference sunlight exhibits a great change (decrease) in irradiance near 950 nm. For this reason, as for the optical filter 9b (whose transmittance adjustment wavelength band ranges from 900 nm to 1000 nm) among the optical filters 9a, 9b, and 9c, the transmission characteristic varies greatly according to the angle of incidence in the vicinity of the incident face of the light guide plate 10. For this reason, there tends to be a great change in spectral coincidence in a wavelength band of around 950 nm.

Therefore, it is preferable that the transmittance adjustment members 13a and 13b adjust at least either a wavelength band including the boundary wavelength (which is here 700 nm) of the wavelength-mixing filter 7 or a wavelength band including a wavelength of around 950 nm where there is a great decrease in irradiance of the reference sunlight. This makes it possible to improve the spectral coincidence in a wavelength band in which there is particularly likely to be a decrease in spectral coincidence.

In this way, the simulated sunlight irradiation apparatus 100 uses the transmittance adjustment members 13a and 13 to control the transmittance of light after emission from the light guide plate 10. However, the directivity of light that is emitted from the light guide plate 10 cannot be completely controlled simply by controlling the transmittance of the light after emission from the light guide plate 10. For this reason, it is difficult to control a spectrum of light after emission.

Therefore, it is preferable that the simulated sunlight irradiation apparatus 100 control the directivity of incoming light before it enters the light guide plate 10. That is, the simulated sunlight irradiation apparatus 100 has the tapered coupler 3 and the optical filter 8 provided between the xenon light source 1 and the light guide plate 10, and has the taper coupler 6 and the optical filter 9 provided between the halogen light source 4 and the light guide plate 10. For this reason, a change in directivity of light entering the light guide plate 10 is small even at the incident end of the light guide plate 10 at which there is likely to be a change in directivity of light that is taken out from the light guide plate 10. This makes it possible to control the transmittance by providing the transmittance adjustment members 13a and 13b. Therefore, a spectrum of light after emission can be easily controlled.

Specifically, as mentioned above, light in a wavelength band of 650 nm to 750 nm around the boundary wavelength of the wavelength-mixing filter 7 is likely to shift in spectrum from the design target. For this reason, the transmittance adjustment members 13a and 13b, which adjust (correct) a shift in transmittance of light in a wavelength band of 650 nm to 750 nm, are provided above the light guide plate 10 near either incident end of the light guide plate 10. This makes it possible to easily adjust the transmittance of light, thus making it possible to control the spectrum even at the incident end of the light guide plate 10. Therefore, a region where the spectral coincidence is high can be extended up to the vicinity of the incident end of the light guide plate 10.

Further, it is preferable that the simulated sunlight irradiation apparatus 100 be designed so that the angle of incidence on the transmittance adjustment members 13a and 13b ranges from 0 degree (normal incidence) to 30 degrees. This causes the directivity of light that is emitted from the light guide plate 10 to be controlled. Therefore, a spectrum of light after emission can be easily controlled.

It should be noted that in the simulated sunlight irradiation apparatus 100, the transmittance adjustment members 13a and 13b are located above the prism sheet 12. However, the transmittance adjustment members 13a and 13b may be located in any other places as long as they are above the irradiation surface of the light guide plate 10. For example, the transmittance adjustment members 13a and 13b may be attached to a back surface of the protective plate 14, which is a member that protects the light guide plate 10.

Further, since the prism sheet 12 applies the effect of refraction of light to create a large number of components of irradiation light that is radiated in a direction perpendicular to the irradiation surface of the light guide plate 10, it is possible to highly precisely adjust spectral distributions by using the optical filters 8 and 9.

Figure 5:
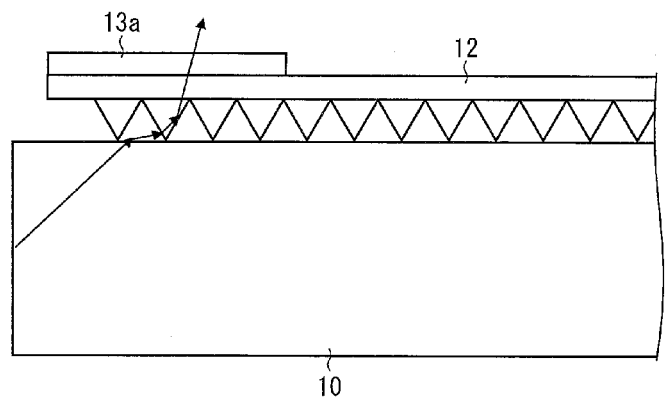
FIG. 5 is a diagram showing how a prism sheet and a transmittance adjustment member are provided in the simulated sunlight irradiation apparatus of FIG. 1.

Furthermore, FIG. 5 is a diagram showing how the prism sheet 12 and each of the transmittance adjustment members 13a and 13b are provided in the simulated sunlight irradiation apparatus 100 of FIG. 1. It is preferable that the prism sheet 12 be shaped as shown in FIG. 5 so that each of its prism has a vertex angle of 60 degrees. This causes more of the light that is radiated from the prism sheet 12 to be directed in a direction perpendicular to the irradiation surface of the light guide plate 10, thus causing more of the light incident on the transmittance adjustment members 13a and 13b to be normally incident. This also heightens the controllability of transmittance by the transmittance adjustment members 13a and 13b.

Figure 6:
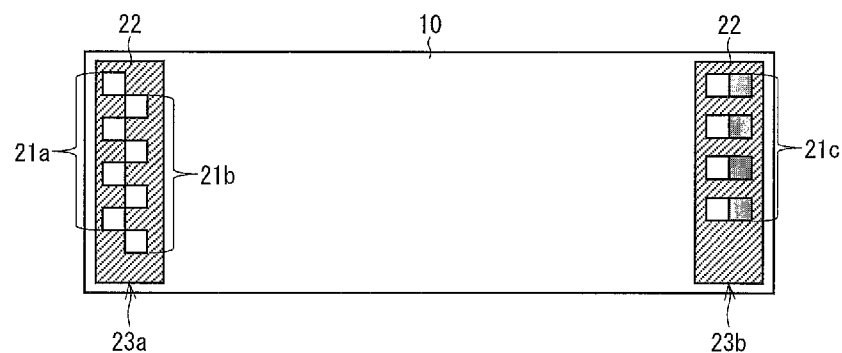
FIG. 6 is a top view showing specific examples of transmittance adjustment members of the simulated sunlight irradiation apparatus of FIG. 1.
Figure 7:
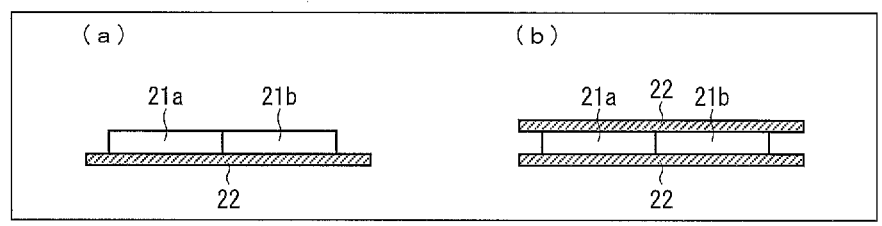
FIG. 7 is a set of cross-sectional views (a) and (b) each showing a configuration of a transmittance adjustment member of FIG. 6.

Meanwhile, in the case of a distribution in which most components of the light incident on the light guide plate 10 have incident angle characteristics of around 30 degrees, there is a sudden change in transmittance of the aforementioned optical filter 9b (Table 1, FIG. 3). This increases the angle dependency of the transmittance by the transmittance adjustment members 13a and 13b. As a result, there is a great shift in transmittance at 30-degree incidence. In this case, it is preferable that the transmittance adjustment members 13a and 13b be able to adjust the transmittance near a wavelength of 950 nm in addition to adjusting the transmittance in a wavelength band (wavelength band of 650 nm to 750 nm) around the boundary wavelength of the wavelength-fixing filter 7. FIGS. 6 and 7 are diagrams each showing a configuration of such transmittance adjustment members 13a and 13b. That is, FIG. 6 is a top view showing specific examples of transmittance adjustment members 23a and 23b of the simulated sunlight irradiation apparatus 100 of FIG. 1. FIG. 7 is a set of cross-sectional views (a) and (b) each showing a configuration of the transmittance adjustment member 23a of FIG. 6.

Specifically, as shown in FIG. 6, the transmittance adjustment member 23a has regions (transmission characteristic regions for different wavelength bands) 21a and 21b provided in substantially identical positions in the vicinity of the light guide plate 10 so as to adjust the transmittances of rays of light in different wavelength bands. Meanwhile, the transmittance adjustment member 23b has a single transmission characteristic region 21c configured to adjust the transmittances of rays of light in different wavelength bands. The transmittance adjustment member 23a is formed such that the regions 21a and 21b, which have different transmittance adjustment wavelength ranges, are arranged in a staggered manner on a silicone sheet 22 serving as a member on which the regions 21a and 21b are arranged. Furthermore, it is preferable that the transmittance adjustment members 23a and 23b be provided on the silicone sheet 22 as shown in FIG. 6 and (a) of FIG. 7. The silicone sheet 22 is low in wavelength dependency of transmission characteristics, and has a viscous surface. This makes it possible to easily place the transmittance adjustment members 23a and 23b without losing the transmission characteristics (transmittance adjustment) of the transmittance adjustment members 23a and 23b, thus making it possible to improve convenience in setting up the transmittance adjustment members 23a and 23b.

Further, the transmittance adjustment member 23a may be configured to be sandwiched between a pair of silicone sheets as shown in (b) of FIG. 7. By thus structuring the silicone sheets 2 to cover the transmittance adjustment member 23a, the transmittance adjustment member 23a can be protected and given a function of transmittance adjustment (a function of adjusting light intensity).

In the simulated sunlight irradiation apparatus 100, as described above, the transmittance adjustment members 13a, 13b, 23a, and 23b adjust the transmittance of light in a portion of a wavelength band of the simulated sunlight that is radiated from the irradiation surface of the light guide plate 10. This causes the spectral coincidence of the simulated sunlight to be improved by the transmittance adjustment members 13a, 13b, 23a, and 23b. This makes it possible to provide a simulated sunlight irradiation apparatus 100 that can radiate simulated sunlight with high spectral coincidence. Further, the simulated sunlight irradiation apparatus 100 can irradiate a large-area object to be irradiated, such as a solar battery panel, with uniform simulated sunlight.

(Another Embodiment of the Simulated Sunlight Irradiation Apparatus 100)

Another embodiment of the simulated sunlight irradiation apparatus 100 is described below with reference to FIGS. 8 through 10. In the following, differences from the simulated sunlight irradiation apparatus 100 are mainly explained, and members having the same functions and effects as those of the simulated sunlight irradiation apparatus 100 are given the same reference signs, and as such, are not described below.

Figure 8:
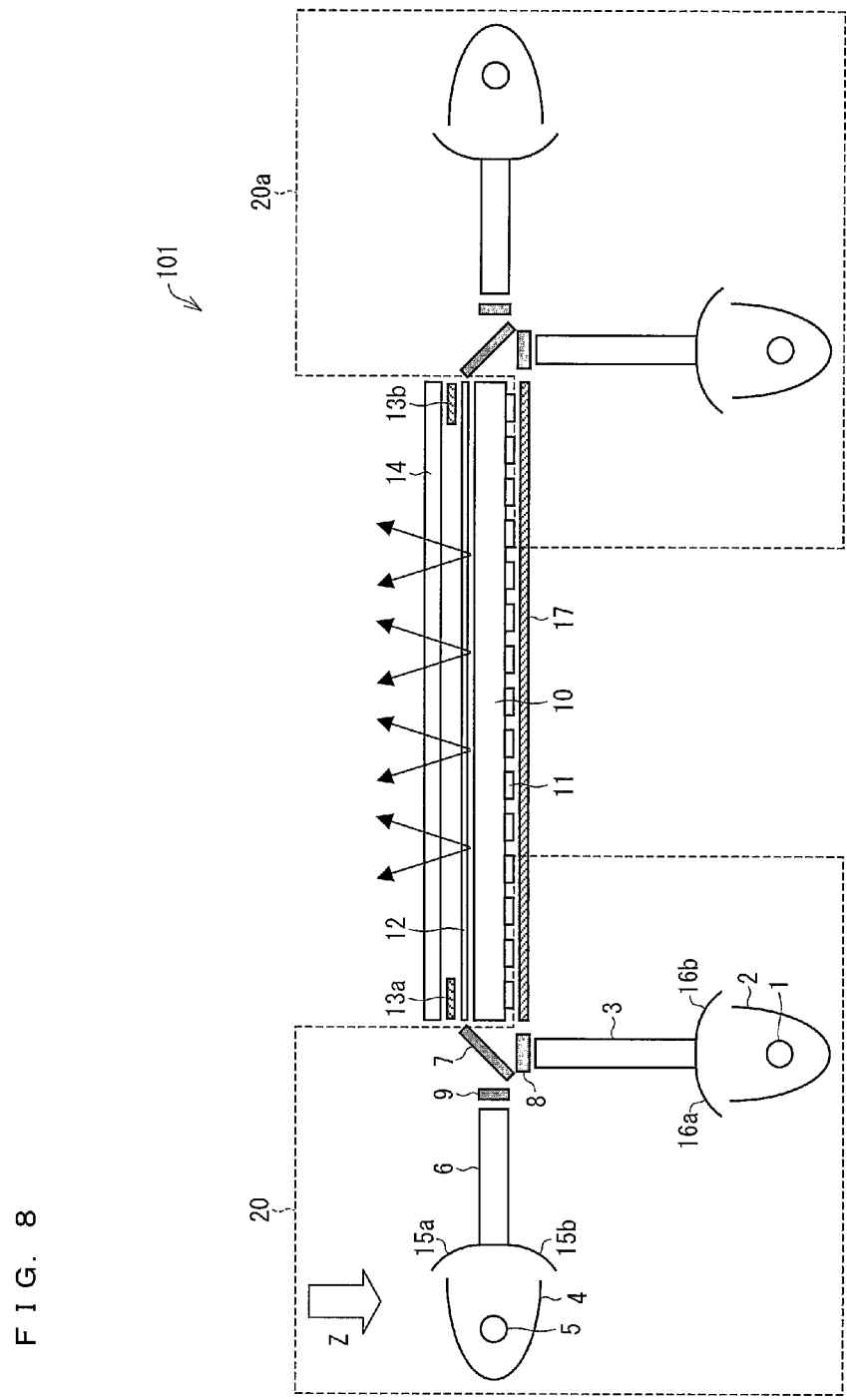
FIG. 8 is a diagram showing a configuration of a main part of a simulated sunlight irradiation apparatus according to another embodiment of the present invention.
Figure 9:
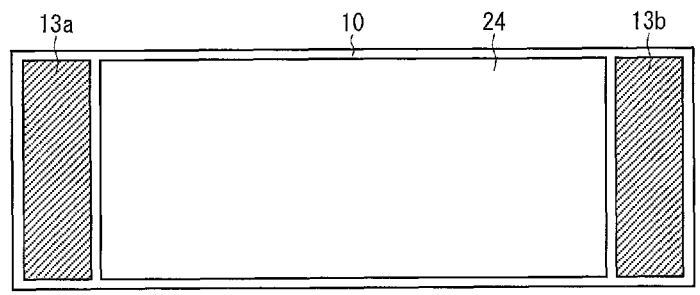
FIG. 9 is a diagram showing how a transparent member is provided in the simulated sunlight irradiation apparatus of FIG. 8.

FIG. 8 is a diagram showing a configuration of a main part of a simulated sunlight irradiation apparatus 101. FIG. 9 is a diagram showing how a transparent member 24 is provided in the simulated sunlight irradiation apparatus 101 of FIG. 8. In addition to the components of the simulated sunlight irradiation apparatus 100, the simulated sunlight irradiation apparatus 101 include a reflective plate (reflector) 17 below the lower surface of the light guide plate 10. This makes it possible to further increase the light intensity (illuminance) of simulated sunlight that is radiated from the light guide plate 10.

Specifically, in the simulated sunlight irradiation apparatus 101, the reflective plate 17 is provided at the side of the light guide plate 10 opposite the irradiation surface. The presence of the reflective plate 17 causes light having entered the reflective plate 17 to be reflected toward the irradiation surface of the light guide plate 10. That is, light emitting from the side of the light guide plate 10 opposite the irradiation surface is reflected by the reflective plate 17, and can be returned toward the irradiation surface by the light extraction section 11. This makes it possible to increase the light intensity of the simulated sunlight irradiation apparatus 101.

However, a light incident end of the light guide plate 10 differs from other parts of the light guide plate 10 in terms of the ratio between light coming in from the light guide plate 10 and reflected by the reflective plate 17 and light coming out directly from the light guide plate 10. This is because, in a case where the reflective plate 17 is formed from a simple mirror-finished surface of a metal such as Al, the metal per se exhibits a wavelength-dependent reflectance. Mixing in of a wavelength-dependent reflected light results in a difference between the proportion in which the light reflected by the reflective plate 17 returns to the irradiation surface near the center of the light guide plate 10 and the proportion in which the light reflected by the reflective plate 17 returns to the irradiation surface near either incident end of the light guide plate 10. This may cause a decrease in spectral coincidence at either incident end of the light guide plate 10.

Specifically, in the case of a reflective plate 17 made of aluminum, the Al reflection characteristic changes around a wavelength of 750 nm. That is, since aluminum has a stable reflectance at a short wavelength (ranging from 300 nm to 700 nm), it is unlikely to suffer from a spectral shift; however, it suffers from a spectral shift at a long wavelength (ranging from 700 nm to 850 nm). In other words, the wavelength band in which the transmittance should be adjusted by the transmittance adjustment members 13a and 13b tends to range from 650 nm to 850 nm. Further, aluminum easily becomes lower in reflectance.

Therefore, it is preferable that the reflective plate 17 have a surface coated with a protective film. For example, it is preferable that the surface of the reflective film 17 is coated with $SiO_2$ or the like so that wavelength dependency is reduced. For example, it is preferable that the reflective plate 17 has a reflectance change of 5% or less in the wavelength band in which the transmittance is adjusted by the transmittance adjustment members 13a and 13b. This makes it possible to reduce the influence (spectral shift) of the change in reflectance by aluminum, thus making it possible to narrow the range of wavelengths in which the transmittance should be adjusted by the transmittance adjustment members 13a and 13b. That is, the control of transmittance by the transmittance adjustment members 13a and 13b can be carried out with finer adjustments. This makes it possible to generate simulated sunlight that is close in emission spectrum to the reference sunlight, without a change in spectral distribution of the simulated sunlight.

Specifically, the proportion in which the reflective plate 17 contributes to the amount of irradiation light from the irradiation surface of the light guide plate 10 is approximately 30%, 5% of which is accounted for by a change in reflectance of the reflective plate 17. The proportion is approximately 30% because it is assumed that 50% of light having entered the light guide plate 10 emits through the side of the light guide plate 10 opposite the irradiation surface (side of an opposite surface of the light guide plate 10 to the irradiation surface) and arrives at the reflective plate 17, that the light having arrived at the reflective plate 17 is attenuated by approximately 10% due to absorption loss by the reflective plate 17, is further attenuated by approximately 10% by reflection loss when passing through the light guide plate 10 again by being reflected by the reflective plate 17, and is kicked out of the irradiation surface by approximately 15%. In this case, the simulated sunlight that is radiated from the light guide plate 10 accounts for approximately 1.5% of the influence on a spectrum change. For this reason, even when the spectral coincidence of the simulated sunlight comes close to a maximal performance level of ±5% (e.g., to Class MS as defined by the JIS), the influence of the reflective plate 17 is acceptable as a vector error. Therefore, it is preferable that the reflective plate 17 has a reflectance change of 5% or less in the wavelength band in which the transmittance is adjusted by the transmittance adjustment members 13a and 13b.

In such a case where the surface of the reflective film 17 is coated with a protective film made of $SiO_2$ or the like, the transmittance adjustment members 13a and 13b can have their rates of transmittance adjustment smaller than in a case where the reflective plate 17 is a mere metal film (not covered with a protective film). For this reason, it is only necessary to improve the spectral coincidence by forming the transmittance adjustment members 13a and 13b only in a part (near either incident end of the light guide plate 10) where there occurs a decrease in spectral coincidence.

It should be noted that the simulated sunlight irradiation apparatuses 100 and 101, provision of the transmittance adjustment members 13a, 13b, 23a, and 23b may cause a great decrease in transmittance of simulated sunlight in the places where they are located. Therefore, it is preferable that a transparent member 24 for irradiance adjustment whose transmission characteristic is substantially uniform with respect to a change in wavelength be provided in a place other than the places where the transmittance adjustment members 13a, 13b, 23a, and 23b are provided. That is, the transmittance adjustment members 13a and 13b (23a and 23b) and the transparent member 24, which has a uniform transmission characteristic, are provided above the irradiation surface of the light guide plate 10. This makes it possible to inhibit a decrease in illuminance of simulated sunlight by the transmittance adjustment members, thus making it possible to reduce nonuniformity in illuminance of simulated sunlight.

Figure 10:
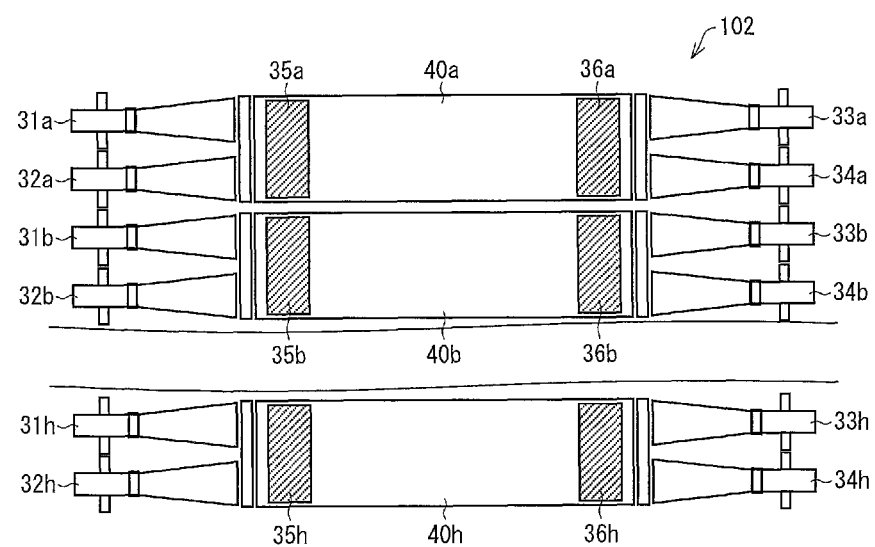
FIG. 10 is a diagram showing a configuration of a main part of a simulated sunlight irradiation apparatus according to still another embodiment of the present invention.

FIG. 10 is a diagram showing a component of a main part of a simulated sunlight irradiation apparatus 102. The simulated sunlight irradiation apparatus 102 includes a plurality of (eight in FIG. 8) light guides 40a to 40h each of which is equivalent to the light guide plate 10 of the simulated sunlight irradiation apparatus 100 or 101. Furthermore, the light guides 40a to 40h each have transmittance adjustment members 35a to 35h and 36a to 36h at both ends thereof, respectively. It should be noted that in FIG. 10, the light guides 40a to 40h are each provided with a plurality of (four in FIG. 10) light introduction sections 31a through 34a to 31h through 34h, respectively, each of which is equivalent to the light introduction section 20 or 20a in shown in FIGS. 1 and 8.

In the case of irradiation of a large area with simulated sunlight, there tends to be a variation in spectral coincidence due to the influence of difference among individual optical elements. In order to counteract this tendency, the simulated sunlight irradiation apparatus 102 is configured to include identical combinations of the light guides 40a to 40h and the plurality of light introduction sections 31a through 34a to 31h through 34h, respectively. Even so, there may be a variation in irradiation spectrum in the vicinity of the incident ends of the light guides 40a to 40h. For this reason, it is preferable that the transmission characteristics of the transmittance adjustment members 35a to 35h and 36a to 36h, which are to be provided for each separate one of the light guides 40a to 40h, be each independently set. Of course, some of the transmission characteristics may be identical to each other. This brings about an increase in spectral coincidence at the incident ends of each of the light guides 40a to 40h. This makes it possible to increase the spectral coincidence even in the case of irradiation of a large area with simulated sunlight. In this way, the simulated sunlight irradiation apparatus 102 is configured to be effective in highly precisely irradiating a large area with simulated sunlight.

As described above, a simulated sunlight irradiation apparatus according to the present invention includes: a first light source which radiates a first ray of light; a second light source which radiates a second ray of light having a spectral distribution that is different from a spectral distribution of the first ray of light; a first optical filter which controls a transmittance of the first ray of light; a second optical filter which controls a transmittance of the second ray of light; a photoselection section which receives the first ray of light whose transmittance has been controlled by the first optical filter and the second ray of light whose transmittance has been controlled by the second optical filter, and which emits simulated sunlight by mixing together a ray of light selected from the first ray of light thus received and a ray of light selected from the second ray of light thus received; a light guide plate which receives the simulated sunlight emitted from the photoselection section; a light extraction section which takes out, to an irradiation surface of the light guide plate, the simulated sunlight received by the light guide plate; and a transmittance adjustment member which is located closer to the irradiation surface of the light guide plate than the light extraction section is, and which adjusts a transmittance of light in a portion of a wavelength band of simulated sunlight that is emitted from the irradiation surface of the light guide plate.

According to the foregoing invention, when the first ray of light emitted from the first light source enters the first optical filter, the transmittance of the first ray of light is controlled by the first optical filter. Similarly, when the second ray of light emitted from the second light source enters the second optical filter, the transmittance of the first ray of light is controlled by the first optical filter. Then, the rays of light, whose transmittances have been controlled by the first and second optical filters, respectively, enter the photoselection section. In this way, emission spectra of the first and second rays of light are adjusted by the first and second optical filters and the photoselection section. As a result, simulated sunlight that is proximate in emission spectrum to reference sunlight is emitted from the photoselection section. Therefore, simulated sunlight that is high in spectral coincidence enters the light guide plate.

Furthermore, according to the foregoing invention, the transmittance adjustment member, located at the side of the irradiation surface of the light guide plate, adjusts a transmittance of light in a portion of a wavelength band of simulated sunlight that is emitted from the irradiation surface of the light guide plate. In this way, the transmittance adjustment member brings about improvement in spectral coincidence of simulated sunlight. This makes it possible to provide a simulated sunlight irradiation apparatus that can radiate simulated sunlight with high spectral coincidence.

The simulated sunlight irradiation apparatus according to the present invention is preferably configured such that the transmittance adjustment member adjusts the transmittance in at least either a wavelength band including a boundary wavelength that is selected by the photoselection section or a wavelength band including a wavelength of 950 nm.

According to the foregoing configuration, the transmittance adjustment member adjusts the transmittance of light in a wavelength band in which there is likely to be a shift in spectral coincidence. This makes it possible to improve the spectral coincidence in a wavelength band in which there is particularly likely to be a decrease in spectral coincidence.

The simulated sunlight irradiation apparatus according to the present invention is preferably configured such that the transmittance adjustment member is provided in the vicinity of an incident face of the light guide plate on which the simulated sunlight is incident.

According to the present invention, the transmittance adjustment member is located in the vicinity of an incident face of the light guide plate where there are likely to be a change in transmittance and a decrease in spectral coincidence. This makes it possible to prevent a decrease in spectral coincidence at the incident face (introduction end) of the light guide plate.

The simulated sunlight irradiation apparatus according to the present invention is preferably configured to further include a directivity control section which controls a directivity of at least either the first ray of light or the second ray of light so that the at least either the first ray of light or the second ray of light enters the photoselection section at a predetermined angle of incidence.

According to the present invention, the directivity control section controls a directivity of at least either the first ray of light or the second ray of light. This causes a ray of light whose transmittance has been controlled to enter the photoselection section at a predetermined angle of incidence. This prevents the first ray of light or the second ray of light from losing its light intensity by the time it arrives at the photoselection section. Furthermore, since the tapered couplers make the ray of light uniform in directivity, it is possible to generate simulated sunlight that is close in spectral distribution to the reference sunlight. This makes it possible to irradiate an irradiated object with simulated sunlight that is close in illuminance (light intensity) and emission spectrum to the reference sunlight.

The simulated sunlight irradiation apparatus according to the present invention is preferably configured such that the directivity control section includes (a) a tapered light guide member which causes the at least either the first ray of light or the second ray of light to enter the photoselection section, and which gradually becomes larger in cross-sectional area from an incident face toward an emitting face and (b) a light-collecting element which causes the at least either the first ray of light or the second ray of light to enter the tapered light guide member.

According to the foregoing invention, the light-collecting element causes the at least either the first ray of light or the second ray of light to enter the tapered light guide member. Furthermore, upon entering the tapered light guide member, the at least either the first ray of light or the second ray of light improves in directivity as it is repeatedly reflected by the side surfaces of the tapered light guide member. This causes a ray of light of uniform directivity (having its angle of radiation controlled) to be emitted from the emitting face of the tapered light guide member. This makes it possible to further improve the directivity of the ray of light.

The simulated sunlight irradiation apparatus according to the present invention is preferably configured to further include a reflector which is provided at the side of an opposite surface of the light guide plate to the irradiation surface, and which reflects, toward the irradiation surface, simulated sunlight emitted from the opposite surface, wherein the reflector has a reflectance change of 5% or less in the wavelength band in which the transmittance is adjusted by the transmittance adjustment member.

According to the foregoing invention, the reflector reflects, toward the irradiation surface, simulated sunlight emitted from the opposite surface of the light guide plate to the irradiation surface. This allows the simulated sunlight to be emitted from the irradiation surface without being lost. Moreover, the reflector is low in wavelength dependency. Therefore, even in a case where the reflector is provided, simulated sunlight that is high in spectral coincidence can be radiated.

It should be noted that the reflectance change can be made 5% or less by coating the reflector with $SiO_2$, which is low in wavelength dependency.

The simulated sunlight irradiation apparatus according to the present invention is preferably configured such that the transmittance adjustment member has a plurality of regions which adjust transmittances of rays of light in different wavelength bands.

According to the foregoing invention, the transmittance adjustment member is provided with a plurality of regions which adjust different ranges of wavelengths. This makes it possible to more suitably adjust the transmittance, thus making it possible to further increase the spectral coincidence.

The simulated sunlight irradiation apparatus according to the present invention is preferably configured such that the transmittance adjustment member is provided on a silicone sheet.

According to the foregoing invention, the transmittance adjustment member is located on the silicone sheet, whose transmission characteristic is low in wavelength dependency. Further, the silicone sheet has a viscous surface. This makes it possible to easily place the transmittance adjustment member without losing the transmission characteristic of the transmittance adjustment member.

The simulated sunlight irradiation apparatus according to the present invention is preferably configured such that the transmittance adjustment member and a transparent member having a uniform transmission characteristic are provided above the irradiation surface of the light guide plate.

According to the foregoing invention, the transmittance adjustment member is provided above the irradiation surface of the light guide plate, and the transparent member is provided above a place on the irradiation surface where the transmittance adjustment member is not provided. This makes it possible to inhibit a decrease in illuminance of simulated sunlight by the transmittance adjustment member, thus making it possible to reduce nonuniformity in illuminance of simulated sunlight.

The simulated sunlight irradiation apparatus according to the present invention is preferably configured such that: the light guide plate includes a plurality of light guides; and the transmittance adjustment member comprises a plurality of transmittance adjustment member provided for each separate one of the light guides.

According to the foregoing invention, the light guide plate includes a plurality of light guides; and the transmittance adjustment member comprises a plurality of transmittance adjustment member provided for each separate one of the light guides. This causes simulated sunlight that is high spectral coincidence to be radiated from each of the light guides. This makes it possible to irradiate a large area with simulated sunlight that is high in spectral coincidence.

The present invention is not limited to the description of the embodiments above, but may be altered by a skilled person within the scope of the claims. An embodiment based on a proper combination of technical means disclosed in different embodiments is encompassed in the technical scope of the present invention. The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention can be used in inspections of, measurements of, and experiments on solar batteries. Further, the present invention can also be used for fading and light-resistance tests on cosmetics, paints, adhesives, and various materials. Furthermore, the present invention can also be used for inspections of and experiments on photocatalysts as well as other various experiments that require natural light.

REFERENCE SIGNS LIST

1 Xenon light source (first light source)
2 Elliptic mirror (directivity control section, light-collecting element)
3 Tapered coupler (directivity control section)
4 Halogen light source (second light source)
5 Elliptic mirror 5 (directivity control section, light-collecting element)
6 Tapered coupler (directivity control section)
7 Wavelength-mixing filter (photoselection section)
8 Optical filter (first optical filter)
9 Optical filter (second optical filter)
9a, 9b, 9c Optical filter (second optical filter)

10 Light guide plate
11 Light extraction section
12 Prism sheet
13a, 13b Transmittance adjustment member
15a, 15b Reflective plate (directivity control section)
16a, 16b Reflective plate (directivity control section)
17 Reflective plate (reflector)
21a, 21b Region (region where transmittance of light is adjusted)
21c Transmission characteristic region (region where transmittance of light is adjusted)
22 Silicone sheet
23a, 23b Transmittance adjustment member
24 Transparent member
31a to 34a, . . . 31h to 34h Light introduction section
35a to 35h Transmittance adjustment member
36a to 36h Transmittance adjustment member
40a to 40h Light guide
100 Simulated sunlight irradiation apparatus
101 Simulated sunlight irradiation apparatus
102 Simulated sunlight irradiation apparatus

The invention claimed is:

1. A simulated sunlight irradiation apparatus comprising:
a first light source which radiates a first ray of light;
a second light source which radiates a second ray of light having a spectral distribution that is different from a spectral distribution of the first ray of light;
a first optical filter which controls a transmittance of the first ray of light;
a second optical filter which controls a transmittance of the second ray of light;
a photoselection section which receives the first ray of light whose transmittance has been controlled by the first optical filter and the second ray of light whose transmittance has been controlled by the second optical filter, and which emits simulated sunlight by mixing together a ray of light selected from the first ray of light thus received and a ray of light selected from the second ray of light thus received;
a light guide plate which receives the simulated sunlight emitted from the photoselection section;
a light extraction section which takes out, to an irradiation surface of the light guide plate, the simulated sunlight received by the light guide plate; and
a transmittance adjustment member which is located closer to the irradiation surface of the light guide plate than the light extraction section is, and which adjusts a transmittance of light in a portion of a wavelength band of simulated sunlight that is emitted from the irradiation surface of the light guide plate.

2. The simulated sunlight irradiation apparatus as set forth in claim 1, wherein the transmittance adjustment member adjusts the transmittance in at least either a wavelength band including a boundary wavelength that is selected by the photoselection section or a wavelength band including a wavelength of 950 nm.

3. The simulated sunlight irradiation apparatus as set forth in claim 1, wherein the transmittance adjustment member is provided in the vicinity of an incident face of the light guide plate on which the simulated sunlight is incident.

4. The simulated sunlight irradiation apparatus as set forth in claim 1, further comprising a directivity control section which controls a directivity of at least either the first ray of light or the second ray of light so that the at least either the first ray of light or the second ray of light enters the photoselection section at a predetermined angle of incidence.

5. The simulated sunlight irradiation apparatus as set forth in claim 4, wherein the directivity control section includes (a) a tapered light guide member which causes the at least either the first ray of light or the second ray of light to enter the photoselection section, and which gradually becomes larger in cross-sectional area from an incident face toward an emitting face and (b) a light-collecting element which causes the at least either the first ray of light or the second ray of light to enter the tapered light guide member.

6. The simulated sunlight irradiation apparatus as set forth in claim 1, further comprising a reflector which is provided at the side of an opposite surface of the light guide plate to the irradiation surface, and which reflects, toward the irradiation surface, simulated sunlight emitted from the opposite surface, wherein
the reflector has a reflectance change of 5% or less in the wavelength band in which the transmittance is adjusted by the transmittance adjustment member.

7. The simulated sunlight irradiation apparatus as set forth in claim 6, wherein the reflector has a surface covered with $SiO_2$.

8. The simulated sunlight irradiation apparatus as set forth in claim 1, wherein the transmittance adjustment member has a plurality of regions which adjust transmittances of rays of light in different wavelength bands.

9. The simulated sunlight irradiation apparatus as set forth in claim 1, wherein the transmittance adjustment member is provided on a silicone sheet.

10. The simulated sunlight irradiation apparatus as set forth in claim 1, wherein the transmittance adjustment member and a transparent member having a uniform transmission characteristic are provided above the irradiation surface of the light guide plate.

11. The simulated sunlight irradiation apparatus as set forth in claim 1, wherein:
the light guide plate includes a plurality of light guides; and
the transmittance adjustment member comprises a plurality of transmittance adjustment member provided for each separate one of the light guides.

* * * * *